(12) United States Patent
Kita et al.

(10) Patent No.: US 6,811,940 B2
(45) Date of Patent: Nov. 2, 2004

(54) MIXED SUBSTANCE OF TRIPHENYLAMINE DIMERS

(75) Inventors: Yoshio Kita, Nishinomiya (JP); Yasuhiro Yamasaki, Neyagawa (JP)

(73) Assignee: Orient Chemical Industries, Ltd., Osaka-fu (JP)

( * ) Notice: Subject to any disclaimer, the term of this patent is extended or adjusted under 35 U.S.C. 154(b) by 3 days.

(21) Appl. No.: 10/246,739

(22) Filed: Sep. 19, 2002

(65) Prior Publication Data

US 2003/0064308 A1 Apr. 3, 2003

(30) Foreign Application Priority Data

Sep. 19, 2001 (JP) ........................................ 2001-284953

(51) Int. Cl.[7] ........................... G03G 5/047; H01B 1/00
(52) U.S. Cl. .................... 430/58.8; 430/59.4; 430/59.5; 430/73; 430/133; 252/500
(58) Field of Search ............... 430/58.8, 59.4, 430/59.5, 133, 73; 252/500

(56) References Cited

U.S. PATENT DOCUMENTS

| | | | |
|---|---|---|---|
| 4,306,008 A | | 12/1981 | Pai et al. |
| 4,988,595 A | * | 1/1991 | Pai et al. ....................... 430/73 |
| 5,910,384 A | * | 6/1999 | Yamasaki et al. ........... 430/59.4 |

FOREIGN PATENT DOCUMENTS

| | | |
|---|---|---|
| EP | 0650955 A1 | 5/1995 |
| GB | 1577237 | 10/1980 |
| JP | 2002-123059 | * 4/2002 |

OTHER PUBLICATIONS

Japanese Patent Office Machine–Assisted Translation of JP 2002–123059 (pub 4/02), Apr. 2002.*

* cited by examiner

*Primary Examiner*—Janis L. Dote
(74) *Attorney, Agent, or Firm*—Birch, Stewart, Kolasch & Birch, LLP

(57) ABSTRACT

The present invention intends to provide a TPD derivative being excellent in electric properties as a compound due to its extremely less content of impurities (TPD analogues) as well as being excellent in film-forming property due to its low crystallinity. The TPD derivative is a mixed substance of triphenylamine dimers which contains at least the compound represented by formula B:

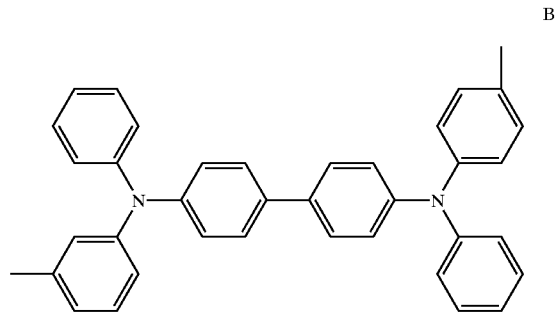

9 Claims, 3 Drawing Sheets 200 um 200 um

MIXED SUBSTANCE OF TRIPHENYLAMINE DIMERS

BACKGROUND OF THE INVENTION

FIELD OF THE INVENTION

The present invention relates to triphenylamine dimer derivatives useful for materials for electrophotographic photoreceptors, organic electroluminescent (EL) materials and the like. Particularly, the present invention relates to a mixed substance of triphenylamine dimers capable of controlling its crystallization during film formation when it is used for a thin film of a charge-transporting layer of a layered type electrophotographic photoreceptor.

Triphenylamine dimer (TPD) derivatives have been used as materials for electrophotographic photoreceptors, organic electroluminescent (EL) materials and the like. Particularly, they are widely employed as charge-transporting materials (CTM) of organic photoreceptors for electrophotography such as copy machines, printers and the like or hole transporting materials (HTM) in EL devices.

In the early stage of research, 4,4-TPD obtained by using 4-methyldiphenylamine as a raw material was used as such a TPD derivative. However, there is a problem that when this is contained practically in a thin film of a charge-transporting layer, crystallization is liable to occur due to symmetrical structure of 4,4-TPD.

When a TPD derivative is used as a component of a layered type photoreceptor, both the electric property of the TPD itself and the film-forming property thereof are both important properties for getting the best electric property. If crystals of TPD are deposited in a film during a drying step and uniformity of the film is lost, the electric property as a photoreceptor is deteriorated obviously.

To solve the problem of poor film forming property of 4,4-TPD, 3,3-TPD obtained by using 3-methyldiphenylamine as a raw material has come to be used widely. That is, by introducing the methyl group into TPD at the m-position, symmetry of 3,3-TPD (compound) is reduced to prevent crystallization when a solvent dries. Further, addition of a small amount of 4,4-TPD to 3,3-TPD is also made for that purpose.

On the other hand, for manufacturing TPD simply in high yield, one of the present inventors has developed a novel method for manufacturing 3,3-TPD (Japanese Patent Laid-Open Publication No. 2000-256276 and U.S. Pat. No. 6,242,648). The 3,3-TPD obtained in this method has high purity and is excellent in electric property as a compound.

However, there has become apparent a new problem in that as the purity of 3,3-TPD becomes higher, crystallinity of the compound also becomes higher unfortunately and if this compound is practically contained in a thin film of a charge-transporting layer, film-forming property is deteriorated.

In other words, the reason why crystallization during film formation has conventionally been controlled by using 3,3-TPD probably is not the substitution with methyl at the 3-position, but probably is that the amine employed as a raw material for condensation, is a mixture of 3-methyldiphenylamine, 3,3'-dimethyldiphenylamine, diphenylamine and the like, and the conventional 3,3-TPD contains a certain amount of TPD analogues by-produced from them. On the other hand, these TPD analogues deteriorate electric properties of an electrophotographic photoreceptor as impurities.

SUMMARY OF THE INVENTION

The objective of the present invention is to provide a TPD derivative being excellent in electric properties as a compound due to its extremely less content of impurities (TPD analogues) as well as being excellent in film-forming property due to its low crystallinity.

The present invention provides a mixed substance of TPDs which comprises at least the compound represented by formula B.

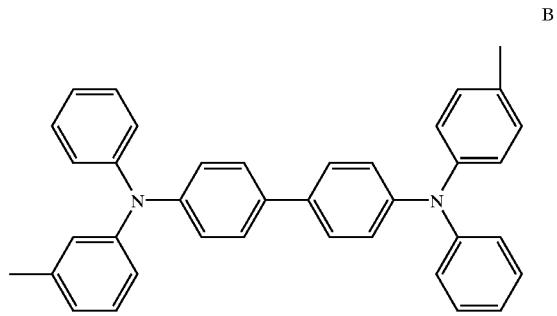

B

The term "mixed substance of TPDs" used in this specification refers to a mixture substantially composed of positional isomers of TPD represented by the chemical formula. Thus, for example the above-mentioned TPD analogs are impurities of the mixed substance of TPDs of the present invention, and it is desirable that the content thereof is as small as possible.

A mixed substance of TPDs of the present invention preferably contains the compound represented by formula A,

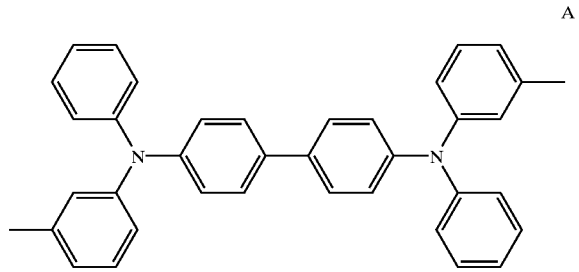

A the compound represented by formula B,

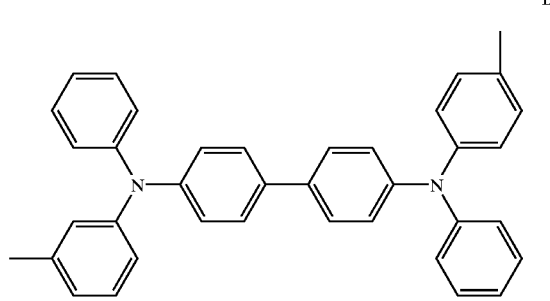

B and the compound represented by formula C.

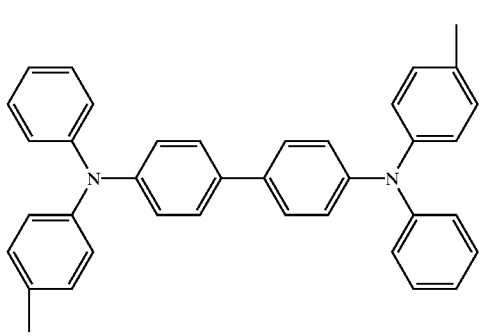

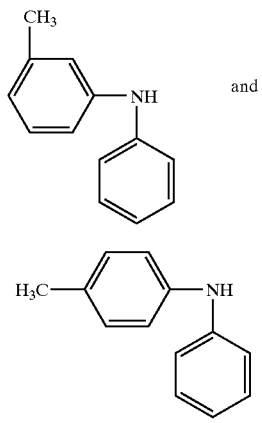

The mixed substance of TPDs of the present invention is excellent in electric properties as a charge-transporting material and has low crystallinity. Thus, when a charge-transporting layer of a layered type electrophotographic photoreceptor is formed by using the mixed substance, a uniform, non-crystalline thin film is provided (see FIG. 2) and a photoreceptor of high sensitivity is provided.

DETAILED DESCRIPTION OF THE INVENTION

Figure 1:
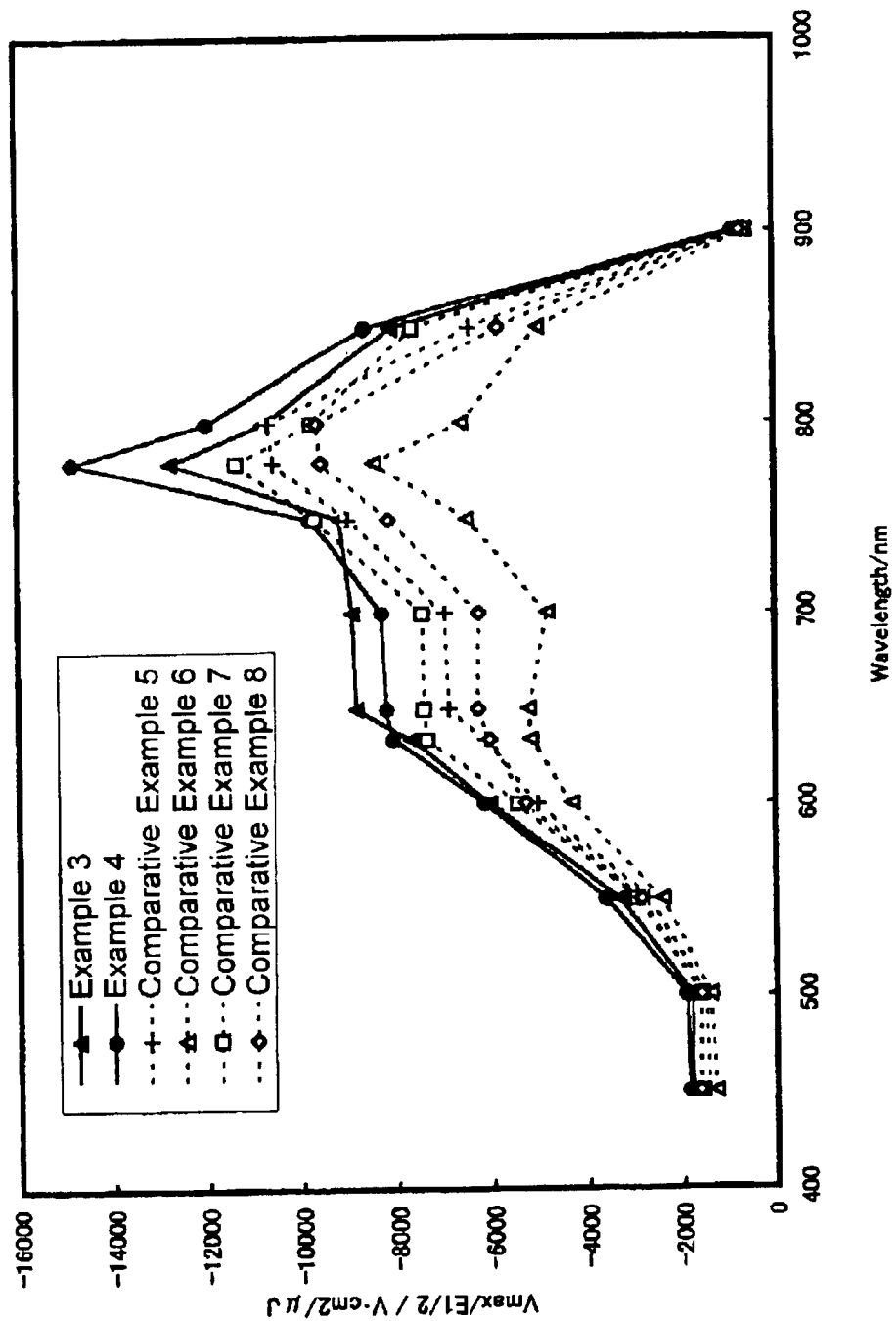
FIG. 1 is a graph showing the spectral sensitivities of the photoreceptor pieces prepared in Examples 3, 4 and Comparative Examples 5, 6, 7 and 8.

The mixed substance of TPDs of the present invention is produced in the same method as that conventionally used for production of TPD except that a mixture of 3-methyldiphenylamine and 4-methyldiphenylamine is used as a raw material for reaction. It is preferable to use a high-pure mixture of 3-methyldiphenylamine and 4-methyldiphenylamine which contains impurities as small as possible. This is for the purpose of controlling formation of the TPD analogues.

More preferably, the mixed substance of TPDs of the present invention is produced in the same method as that described in Japanese Patent Laid-Open Publication No. 2000-256276 where an Ullmann reaction is employed.

That is, 4,4'-dihalobiphenyl, preferably, 4,4'-diiodobiphenyl represented by the following formula (1) is obtained.

Next, a raw material amine mixture is obtained. The raw material amine mixture is, as described above, a mixture of 3-methyldiphenylamine represented by the following formula (2) and 4-methyldiphenylamine represented by the following formula (3).

Each purity of 3-methyldiphenylamine and 4-methyldiphenylamine is preferably 97.5% by weight or more, more preferably 99% by weight or more. If 3-methyldiphenylamine or 4-methyldiphenylamine has a purity of 95% by weight or less, formation amounts of the TPD analogues will increase and electric properties of the resulting TPD will be deteriorated.

The 3-methyldiphenylamine and the 4-methyldiphenylamine are mixed in a molar ratio of preferably from about 75:25 to about 95:5, more preferably from about 90:10 to about 95:5. If the combination amount of 4-methyldiphenylamine is more than 25% by mol based on the amine mixture, 4,4-TPD is formed in large amount and crystallization readily occurs during the formation of a charge-transporting film in a photoreceptor. If the combination amount of 4-methyldiphenylamine is less than 5% by mole based on the amine mixture, the formation ratios of 3,4-TPD and 4,4-TPD are low and it becomes difficult to obtain an objective mixed substance of TPDs.

Next, the above-mentioned amine mixture is allowed to react with 4,4'-diiodobiphenyl in the presence of a base, a copper catalyst and a reaction promoter (e.g., polyethylene glycol).

In the reaction, as in the case of known Ullmann reactions, as a base, alkali metal hydroxides such as potassium hydroxide and sodium hydroxide; alkali metal carbonates such as potassium carbonate and sodium carbonate; trialkylamines such as triethylamine and triisopropylamine; and metal alkoxides such as tert-BuONa and tert-BuOK are exemplified. From the viewpoint of production cost (yield and cost of raw materials), potassium carbonate is particularly preferred. Metal copper (Cu(0)) is used as the copper catalyst. The amount of the base and the copper catalyst may be the same as those employed in conventional Ullmann reactions.

Polyethylene glycol or polyethylene glycol diether is used as a reaction promoter or a reaction solvent. Preferable polyethylene glycol includes diethylene glycol, triethylene glycol, tetraethylene glycol and polyethylene glycol, or their mixtures and the like. Specifically, PEG-6000 (trade name) manufactured by Wako Pure Chemical Industries K.K. can be used. As polyethylene glycol diether, for example, diethylene glycol dimethyl ether (diglyme), triethylene glycol dimethyl ether (triglyme), tetraethylene glycol dimethyl ether (tetraglyme), polyglyme and their mixtures, diethylene glycol diethyl ether, and diethylene glycol methyl ethyl ether and the like are exemplified. Specifically, PMP400 (trade name) manufactured by Toho Chemical Industry K.K. can be used.

The amount of a reaction promoter to be used is from 1/10 to 10 times, preferably from 1/10 to 1/5 times by weight based on the weight of 4,4'-diiodobiphenyl.

The reaction between 4,4'-diiodobiphenyl and the amine mixture (N-arylation reaction) may be carried out using, as a reaction solvent, polyethylene glycol or polyethylene glycol diether, which is a reaction promoter, or may be carried out using other proper reaction solvents. It may also be carried out without using any solvent. The reaction procedure generally comprises charging 4,4'-diiodobiphenyl, a raw material amine mixture, a base (preferably potassium carbonate), a copper catalyst, a reaction promoter and, optionally, a reaction solvent into a proper vessel and stirring for 5 to 40 hours while holding at 100 to 250° C.

The progress of the reaction can be traced by conventional methods such as chromatography. After the completion of the reaction, the solvent is removed by distillation and products are separated and purified by conventional methods such as chromatography. The products can be identified by elementary analysis, MS (FD-MS) analysis, IR analysis, $^1$H-NMR and $^{13}$C-NMR.

Next described is a typical example of the process of the production of the mixed substance of TPDs of the present invention.

To a mixture of 3-methyldiphenylamine and 4-methyldiphenylamine in a molar ratio of about 90:10 to 95:5, a copper catalyst (copper powder) is added and heated to about 30° C. To the resulting mixture, 4,4'-diiodobiphenyl and polyethylene glycol (PEG) as a reaction promoter are added and heated to 100° C. Then, powdery potassium carbonate is added, heated to 205° C. and stirred for 14 hours.

After standing to cool, DMF is added and stirred at 130° C. for 1 hour. After additional standing to cool to 90° C., hot water is added to the resulting mixture and is stirred for additional 2 hours. After filtration, the resulting cake is washed with hot water to obtain brown solid.

Purification is carried out by dispersing and stirring the resulting brown solid in DMF for about 1 hour and then separating solid by filtration.

The resulting cake is further washed with DMF and methanol. After refluxing the resulting solid together with active carbon in xylene for about 1 hour, the mixture is allowed to cool to 70° C. and subsequently is filtered.

The filtrate is passed through a column filled with an absorbent to obtain a colorless, transparent solution. The solvent is removed by distillation under reduced pressure. The crystals deposited are collected by filtration and dried to obtain a composition of positional isomeric TPDs of the present invention in high yield.

The mixed substance of TPDs produced in this method theoretically is a mixture of three kinds of TPD derivatives represented by formulae A, B and C above.

The formation ratio of the above three TPD derivatives is about 81:18:1 according to the probability when the compounding ratio of 3-methyldiphenylamine and 4-methyldiphenylamine is 90:10 by mol, and is 90.25:9.5:0.25 when the compounding ratio of 3-methyldiphenylamine and 4-methyldiphenylamine is 95:5 by mol.

4,4-TPD (formula C) is liable to form crystals because of its symmetrical structure. Therefore, amorphism of a charge-transporting film may be impaired in the case when content of the 4,4-TPD is high level. However, according to the above described process, the formation probability of 4,4-TPD is 10% or several percent or less in the mixed substances of TPDs, and amorphism of the film is not impaired.

Next, examples of the application of the mixed substance of TPDs obtained in the method of the present invention for layered type electrophotographic photoreceptors will be described.

An electrophotographic photoreceptor is a device such that when a beam light corresponding to an image is applied thereto, a latent image consisting of charges is formed on the surface where the light is received. An organic electrophotographic photoreceptor comprises an organic photoconductive material on a conductive support. The organic photoconductive material is a material formed by binding a photoconductive compound with a resin.

In general, as electrophotographic photoreceptors, layered type photoreceptors are widely employed. The layered type photoreceptor comprises a charge-generating layer containing a charge-generating material, such as phthalocyanines, which generates charges when light is applied thereto, and a charge-transporting layer containing a charge-transporting material which transports charges to a surface region of the photoreceptors.

TPD derivatives are useful as charge-transporting materials of electrophotographic photoreceptors which are employed widely in copy machines or the like employing the electrophotography technology. Particularly, the mixed substance of TPDs of the present invention provides photoreceptors having good electrostatic property and also having medium or high sensitivity and high durabilities (durabilities with respect to sensitivity and potential) when it is used in a charge-transporting layer of an organic photoreceptor in combination with phthalocyanine-type charge-generating materials such as titanyl phthalocyanine, $\mu$-oxo-aluminum phthalocyanine dimer and $\mu$-oxo-gallium phthalocyanine dimer.

Such a function separation type photoreceptor is formed, for example, by laying a charge-generating layer and a charge-transporting layer, both being in the form of a thin film, onto a conductive support. Metal such as aluminum and nickel, metallized films and the like can be used as a substrate of the conductive support. The substrate may be produced in the form of drum, sheet or belt.

The TPD derivatives may be applied to the organic photoreceptors for electrophotography such that a charge-generating layer containing a photoconductive phthalocyanine pigment as a charge-generating material is formed in the form of a thin film on a conductive support. The charge-generating layer is generally formed by preparing an application liquid in which a charge-generating material is dispersed in a solution of a binding resin dissolved in a solvent, and subsequent applying the application liquid onto a conductive support. However, the charge-generating layer may be formed by vapor deposition of a phthalocyanine pigment onto a conductive support to form a thin film.

The phthalocyanine pigments may be dispersed in the method conventionally known to the art by using a ball mill, a sand mill, a paint shaker and the like.

The means for applying a charge-generating layer is not particularly limited. For example, a bar coater, a dip coater, a spin coater, a roller coater and the like can properly be used. Drying can be carried out at a temperature of 30 to 200° C. for a period of 5 minutes to 2 hours, at rest or under ventilation.

The solvent for the application liquid is not particularly limited on condition that the phthalocyanine pigment is uniformly dispersed without being dissolved and the binding resin optionally used is dissolved. Examples thereof include alcoholic solvents such as methanol, ethanol, isopropanol and butanol; aromatic solvents such as toluene, xylene and tetralin; halogen-containing solvents such as dichloromethane, chloroform, trichloroethylene and carbon tetrachloride; ester solvents such as ethyl acetate and propyl acetate; ether solvents such as ethylene glycol monoethyl ether, dioxane and tetrahydrofuran; ketone solvents such as cyclohexanone, methyl ethyl ketone and methyl isobutyl ketone; dimethylformamide, dimethyl sulfoxide and the like.

The binding resin can be selected from a wide range of insulating resins. Preferred resins include condensation-type resins such as polycarbonate, polyester, polyamide and polyarylate; addition polymerizates such as polystyrene, polyacrylate, styrene-acrylic copolymers, polyacrylamide, polymethacrylate, polyvinyl butyral, polyvinyl alcohol, polyacrylonitrile, polyacryl-butadiene copolymers, polyvinyl chloride and vinyl chloride-vinyl acetate copolymers; organic photoconductive resins such as poly-N-vinylcarbazole and polyvinylanthracene; polysulfone, polyether sulfone, silicone resins, epoxy resins and urethane resins. These may be used in proper combination.

The binding resin is employed in an amount of 0.1 to 3 ratio by weight based on the weight of the charge-generating material. If the amount is greater than 3 ratio by weight, concentration of the charge-transporting material in the charge-generating layer becomes small and photosensitivity becomes poor. The charge-generating layer generally has a thickness of 10 μm or less, preferably from 0.05 to 5.0 μm.

Next, a charge-transporting layer containing a charge-transporting material is formed in the form of a thin film on the charge-generating layer. The charge-transporting layer may be applied in the same manner as that described for the charge-generating layer. The thin film can be formed, for example by dissolving a charge-transporting material in a solvent optionally together with a binding resin, applying the resulting solution uniformly onto the charge-generating layer and then drying.

As the charge-transporting material, the mixed substance of TPDs obtained in the method of the present invention is used. As the binding resin and the solvent for forming the charge-transporting layer, the same materials as that described for the charge-generating layer can be used.

The binding resin is employed in an amount of from 0.1 to 5 ratio by weight based on the weight of the charge-transporting material. If the amount is greater than 5 ratio by weight, concentration of the charge-transporting material in the charge-transporting layer becomes small and photosensitivity becomes poor. The charge-transporting layer generally has a thickness of 100 μm or less, preferably from 5 to 50 μm.

The following Examples further illustrate the present invention in detail but are not to be construed to limit the scope thereof.

EXAMPLE 1

Synthesis of Mixed Substance of TPDs

To 5000-ml four-neck flask, 438 g (2.43 mol) of 3-methyldiphenylamine and 49 g (0.27 mol) of 4-methyldiphenylamine (molar ratio=90:10) were fed. 28 g (4.4 mol) of copper powder was added thereto and was heated to 30° C. To the mixture, 450 g (1.1 mol) of 4,4'-diiodobiphenyl and 47 g of PEG6000 were added. After heating to 100° C. and adding 307 g (2.2 mol) of powdery potassium carbonate, the resulting mixture was heated to 205° C. and stirred for 14 hours. After standing to cool, DMF was added and stirred for 1 hour at 130° C. After standing to cool to 90° C., hot water was added to the resulting mixture and was stirred for additional 2 hours. After filtration, the cake was washed with hot water to obtain a brown solid. The resulting brown solid was dispersed and stirred in DMF for 1 hour and then collected by filtration. Further, the resulting cake was washed with DMF and methanol. The resulting solid was refluxed together with active carbon in xylene for 1 hour, subsequently allowed to cool to 70° C. and then filtered. The filtrate was passed through a column filled with an absorbent to obtain a colorless transparent solution. The solvent was removed by distillation under reduced pressure. The crystals deposited were collected by filtration and were dried to obtain 455 g of the mixed substance of TPDs.

EXAMPLE 2

Synthesis of Mixed Substance of TPDs 457 g of the mixed substance of TPDs was obtained in the same manner as that described in Example 1 except that the mixing ratio of 3-methyldiphenylamine to 4-methyldiphenylamine was changed to 95:5 by mol.

EXAMPLE 3

Preparation of Layered Type Photoreceptor Piece

In a 100-ml mayonnaise bottle, 0.2 g of Y-type titanyl phthalocyanine (a product obtained by the manner as described in Japanese Patent Laid-Open Publication No. H3(1991)-35064), 0.2 g of the polyvinyl butyral resin (trade name: Elex BH-3, manufactured by Sekisui Chemical K.K.), 59.6 g of cyclohexanone and 50 g of 3 mm φ glass beads were added and shaken with a paint shaker for 1 hour. The resultant was formed into a film to have a thickness of 0.5 μm on an aluminum plate washed well with acetone by use of a bar coater No. 6. Thereby, a charge-generating layer was formed. Further, a solution obtained by dissolving 1.0 g of the mixed substance of TPDs synthesized in Example 1 and 1.0 g of polycarbonate (trade name: Panlite L-1250, manufactured by Teijin K.K.) in 11.3 g of dichloromethane was formed into a film to have a thickness of 20 μm on the charge-generating layer by use of a bar coater No. 32. Thereby, a charge-transporting layer was formed. Thus, layered type photoreceptor was prepared.

EXAMPLE 4

Preparation of Layered Type Photoreceptor Piece

A layered type photoreceptor piece was prepared in the same manner as that described in Example 3 except that the mixed substance of TPDs synthesized in Example 2 was used.

Comparative Example 1

Synthesis of 3,3-TPD (Method described in Japanese Patent Laid-Open Publication No. 2000-256276)

To a 100-ml four-neck glass flask, 1.0 g (2.46 mmol) of 4,4'-diiodobiphenyl and 20 ml of o-dichlorobenzene were added. Further, 1.08 g (5.90 mmol) of 3-methyldiphenylamine, 0.104 g of polyethylene glycol (PEG-6000 (trade name) manufactured by Wako Pure Chemical Industries K.K.) as a reaction promoter, 2.73 g (0.0198 mol) of potassium carbonate and 0.635 g (9.87 mmol) of copper (powder) were added and refluxed under stirring. The reaction was traced by high-performance liquid ion chromatograph and the refluxing was continued under stirring until the peaks of the raw materials and intermediates had disappeared (for 22 hours). After hot filtration, the product was washed with dichloromethane until the color of the filtrate had become light and then the solvent was removed under reduced pressure. The residue was purified by silica gel chromatography to obtain 1.01 g of N,N'-diphenyl-N,N'-ditolyl-4,4'-diaminobiphenyl (3,3-TPD) (yield=78.7%).

Comparative Example 2

Synthesis of 4,4-TPD 4,4-TPD was synthesized in the same manner as that described in Comparative Example 1 except that 4-methyldiphenylamine was used in place of 3-methyldiphenylamine.

mixture of TPD prepared in Comparative Example 3 was used in place of the mixed substance of TPDs.

Comparative Example 8

A photoreceptor piece was prepared in the same manner as that described in Example 3 except that the simple mixture of TPD prepared in Comparative Example 4 was used in place of the mixed substance of TPDs.

(Test of Electric Properties)

The organic photoreceptor property and the spectral sensitivity were measured by using an electrostatic paper analyzer (trade name: EPA-8200, manufactured by Kawaguchi Electric Works K.K.). The results are shown in Table 1.

TABLE 1

| | Conditions of TPD synthesis | $V_{max}$ (V) | Dark decay rate (%) | Half decay exposure sensitivity (Lx.s) | Residual potential (V) |
|---|---|---|---|---|---|
| Example 3 | 3-MPA:4-MPA = 90:10 | −580 | −22.3 | 1.12 | −2.3 |
| Example 4 | 3-MPA:4-MPA = 95:5 | −634 | −23.2 | 1.07 | −3.0 |
| Comp. Example 5 | 3-MPA = 100% | −587 | −22.1 | 1.12 | 0 |
| Comp. Example 6 | 4-MPA = 100% | −498 | −28.6 | 0.90 | −1.7 |
| Comp. Example 7 | 3,3-TPD (90%) + 4,4-TPD (10%) | −475 | −29.9 | 1.05 | −2.3 |
| Comp. Example 8 | 3,3-TPD (95%) + 4,4-TPD (5%) | −624 | −20.1 | 1.20 | −9.3 |

MPA: Methyldiphenylamine

Comparative Example 3

A simple mixture of TPD was obtained by mixing 3,3-TPD synthesized in Comparative Example 1 and 4,4-TPD synthesized in Comparative Example 2 by mol of 90:10.

Comparative Example 4

A simple mixture of TPD was obtained by mixing the 3,3-TPD synthesized in Comparative Example 1 and the 4,4-TPD synthesized in Comparative Example 2 by mol of 95:5.

Comparative Example 5

A photoreceptor piece was prepared in the same manner as that described in Example 3 except that the 3,3-TPD synthesized in Comparative Example 1 was used in place of the mixed substance of TPDs.

Comparative Example 6

A photoreceptor piece was prepared in the same manner as that described in Example 3 except that the 4,4-TPD synthesized in Comparative Example 2 was used in place of the mixed substance of TPDs.

Comparative Example 7

A photoreceptor piece was prepared in the same manner as that described in Example 3 except that the simple The graphs of spectral sensitivity of Examples 3 and 4 and Comparative Examples of 5, 6, 7 and 8 are shown in FIG. 1.

Considerations: In the graphs of spectral sensitivity, Examples 3 and 4 are relatively high, whereas Comparative Examples 7 and 8 which employ the simple mixture of TPD are relatively low. As to Comparative Example 6, the poor sensitivity is probably due to impaired uniformity of the film caused by crystallization of 4,4-TPD which has good symmetrical structure. In Comparative Example 5, conventional 3,3-TPD was used and properties corresponding thereto were shown.

(Film-Forming Property)

The photoreceptor piece used for the test of electric properties was stripped off from the aluminum plate and was observed with an optical microscope BX60 (OLYMPUS; magnifications: eye lens=×10, object lens=×10) equipped with a digital camera HC2500 (FUJIX) using transmitted light. Analysis and print were carried out by using the image analysis software "analy SIS 3.1 (Soft-imaging System)".

Figure 2:
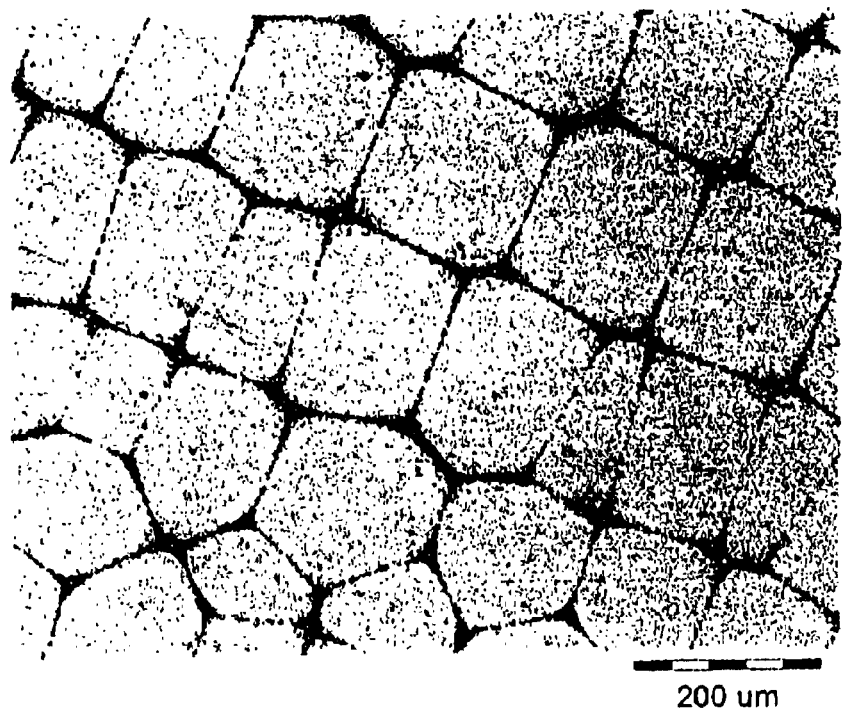
FIG. 2 is a microphotograph showing crystallization condition of the charge-transporting layer of the photoreceptor obtained in Example 4.
Figure 3:
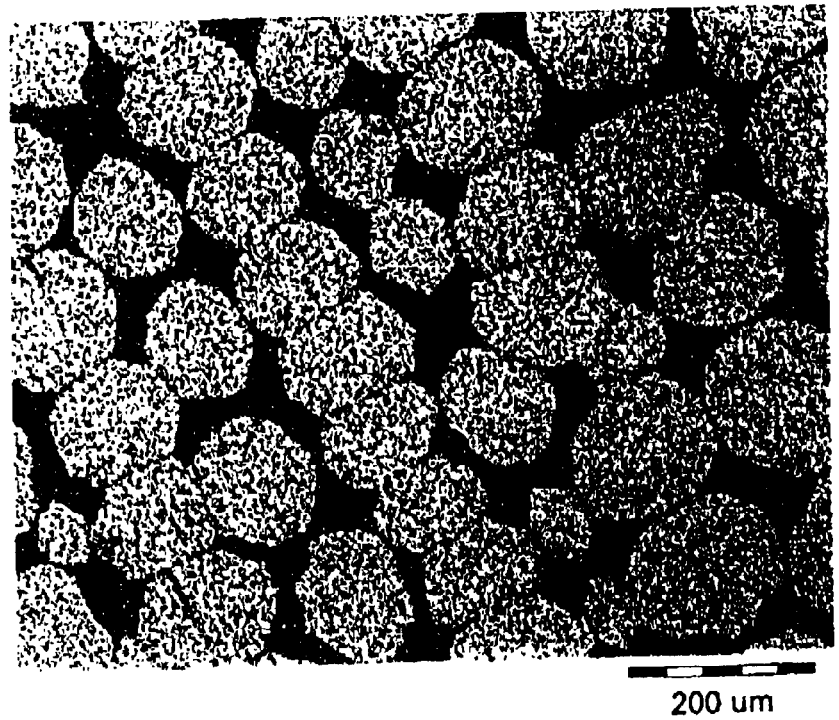
FIG. 3 is a microphotograph showing crystallization condition of the charge-transporting layer of the photoreceptor obtained in Comparative Example 5.
Figure 4:
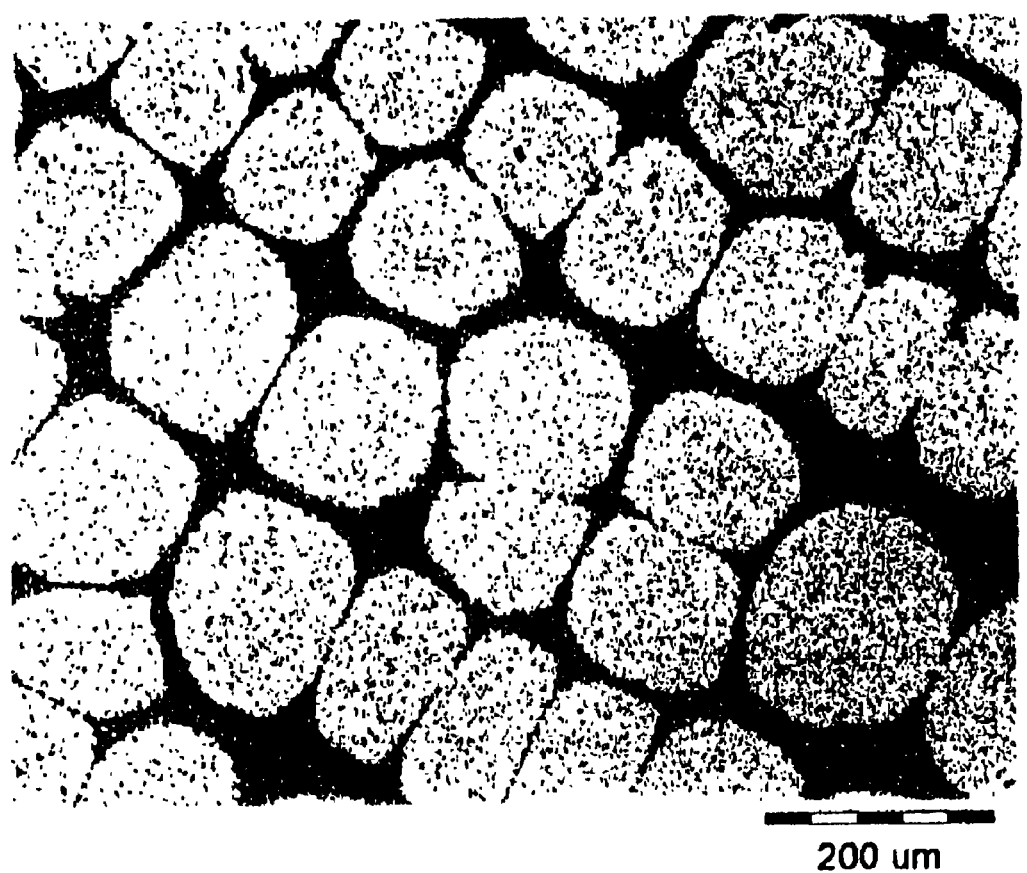
FIG. 4 is a microphotograph showing crystallization condition of the charge-transporting layer of the photoreceptor obtained in Comparative Example 8.

The microphotographs (magnification: ×100) obtained with respect to the photoreceptors of Example 4 and Comparative Examples 5 and 8 are shown in FIGS. 2, 3 and 4, respectively. In the photographs, black parts are crystalline parts where crystallization occurred.

Considerations: In Example 4 (FIG. 2), there are at least some crystalline parts, but remarkable improvement was observed by comparison with Comparative Example 5 (FIG. 3). In Comparative Example 8 (FIG. 4), a considerable improvement was observed by comparison with Comparative Example 5 (FIG. 3), but is not satisfactory.

What is claimed is:

1. A mixed substance of triphenylamine dimers which comprises at least the compound represented by formula B

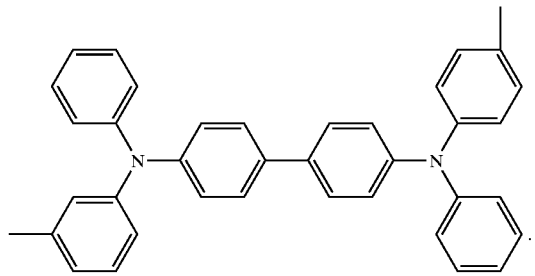

2. A mixed substance of triphenylamine dimers which comprises the compound represented by formula A

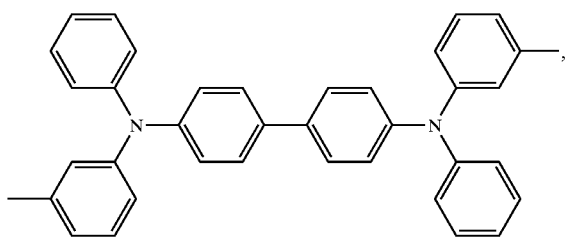

the compound represented by formula B

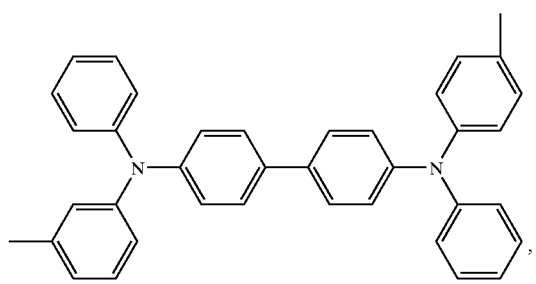

and the compound represented by formula C

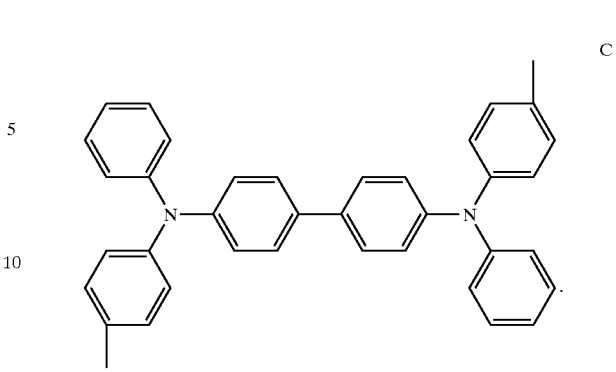

3. A mixed substance of triphenylamine dimers which is obtained by allowing a mixture of 3-methyldiphenylamine and 4-methyldiphenylamine to react with 4,4'-dihalobiphenyl.

4. The mixed substance of triphenylamine dimers according to claim 3, wherein the 3-methyldiphenylamine and the 4-methyldiphenylamine are mixed in a molar ratio of 75:25 to 95:5.

5. A charge-transporting material for a layered electrophotographic photoreceptor which comprises the mixed substance of triphenylamine dimers according to any one of claims 1 to 4.

6. A charge-transporting layer for a layered electrophotographic photoreceptor which comprises the mixed substance of triphenylamine dimers according to any one of claims 1 to 4 and a binder resin.

7. A process for forming a charge-transporting layer for a layered electrophotographic photoreceptor comprising the steps of:
dissolving the mixed substance of triphenylamine dimers according to any one of claims 1 to 4 in a solvent together with a binding resin;
applying the resulting solution uniformly onto a charge-generating layer, and
drying the resulting coated layer.

8. A layered electrophotographic photoreceptor which comprises a conductive support, a charge-generating layer and a charge-transporting layer, wherein the charge-transporting layer comprises the mixed substance of triphenylamine dimers according to any one of claims 1 to 4 as a charge-transporting material.

9. The layered electrophotographic photoreceptor according to claim 8, wherein the charge-generating layer comprises, as a charge-generating material, a phthalocyanine compound selected from the group consisting of titanyl phthalocyanine, $\mu$-oxo-aluminum phthalocyanine dimer and $\mu$-oxo-gallium phthalocyanine dimer.

* * * * *